US012725700B2

(12) United States Patent
Pitchers

(10) Patent No.: US 12,725,700 B2
(45) Date of Patent: Sep. 1, 2026

(54) EQUIPMENT MONITORING SYSTEM

(71) Applicant: KONINKLIJKE PHILIPS N.V., Eindhoven (NL)

(72) Inventor: Stephen Michael Pitchers, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 205 days.

(21) Appl. No.: 18/689,898

(22) PCT Filed: Aug. 26, 2022

(86) PCT No.: PCT/EP2022/073778
§ 371 (c)(1),
(2) Date: Mar. 7, 2024

(87) PCT Pub. No.: WO2023/041307
PCT Pub. Date: Mar. 23, 2023

(65) Prior Publication Data
US 2024/0371507 A1 Nov. 7, 2024

(30) Foreign Application Priority Data
Sep. 14, 2021 (EP) .................................... 21196645

(51) Int. Cl.
*G16H 40/40* (2018.01)
*G16H 40/67* (2018.01)

(52) U.S. Cl.
CPC ............ *G16H 40/40* (2018.01); *G16H 40/67* (2018.01)

(58) Field of Classification Search
CPC .............................. G16H 40/40; G16H 40/67
USPC .......................................................... 705/2–3
See application file for complete search history.

(56) References Cited

U.S. PATENT DOCUMENTS 5,759,199 A * 6/1998 Snell .................. A61N 1/37247 128/903
2007/0253021 A1* 11/2007 Mehta ................. H04L 61/5038 382/128
2009/0119282 A1* 5/2009 Load ...................... G16H 70/60 707/999.005
2012/0191826 A1* 7/2012 Gotesdyner ......... H04L 12/6418 709/221
2013/0031201 A1* 1/2013 Kagan .................... G01D 4/004 709/213
2013/0194106 A1* 8/2013 Lee .................... A61N 1/37223 340/870.3

(Continued)

FOREIGN PATENT DOCUMENTS

EP 3030996 B1 3/2019
WO 2020/0254452 A1 12/2020

OTHER PUBLICATIONS

International Search Report and Written Opinion Dated Nov. 23, 2022 For International Application No. PCT/EP2022/073778 Filed Aug. 26, 2022.

*Primary Examiner* — Michael Tomaszewski

(57) ABSTRACT

Provided is an equipment monitoring system. The equipment monitoring system receives first telemetry information from a medical device and determines, based on the first telemetry information, whether the device has a configuration error. If the device is determined to have a configured error, the system obtains second telemetry information from the device to confirm whether the device has a configuration error.

11 Claims, 4 Drawing Sheets

(56) References Cited

U.S. PATENT DOCUMENTS

| | | | | |
|---|---|---|---|---|
| 2014/0129248 | A1* | 5/2014 | Zuehlsdorff | G16H 40/20 705/2 |
| 2014/0249831 | A1* | 9/2014 | Gallopyn | G16H 40/20 705/2 |
| 2015/0227838 | A1* | 8/2015 | Wang | G16H 40/40 706/12 |
| 2016/0352608 | A1* | 12/2016 | Cornell | H04L 43/10 |
| 2017/0216611 | A1* | 8/2017 | Yoder | A61N 1/37217 |
| 2017/0296056 | A1* | 10/2017 | Hresko | G16H 40/40 |
| 2018/0083841 | A1* | 3/2018 | Mutreja | H04L 41/0806 |
| 2018/0140271 | A1* | 5/2018 | Raman | A61B 6/545 |
| 2019/0015668 | A1* | 1/2019 | Marnfeldt | A61N 1/37217 |
| 2019/0318039 | A1* | 10/2019 | Nozhchev | G06F 16/256 |
| 2019/0319839 | A1* | 10/2019 | Nozhchev | H04L 41/40 |
| 2019/0377630 | A1* | 12/2019 | Noyes | G06F 11/1076 |
| 2020/0245170 | A1* | 7/2020 | Minai | H04W 28/04 |
| 2022/0036980 | A1* | 2/2022 | Beranek | G16H 40/40 |
| 2024/0371507 | A1* | 11/2024 | Pitchers | G06F 11/3013 |

* cited by examiner

EQUIPMENT MONITORING SYSTEM

CROSS REFERENCE TO RELATED APPLICATIONS

This application is the U.S. National Phase application under 35 U.S.C. § 371 of International Application No. PCT/EP2022/073778 filed Aug. 26, 2022, which claims the benefit of European Patent Application Number 21196645.2 filed Sep. 14, 2021. These applications are hereby incorporated by reference herein.

FIELD OF THE INVENTION

This invention relates to an equipment monitoring system and associated method for monitoring equipment, in particular medical devices including medical imaging devices.

BACKGROUND OF THE INVENTION

Large medical facilities, such as hospitals, make use of a variety of medical devices. A common and complex subset of these are imaging devices, used in techniques such as Computed Tomography/Positron Emission Tomography, Magnetic Resonance imaging, Image Guided Therapy, Digital X-Ray/Radiography, interventional X-Ray, Nuclear Medicine/Advanced Molecular Imaging, Electrophysiology and Ultrasound. The devices used for these imaging techniques require regular servicing, management and upgrades to function properly. For example, old components may need to be replaced and software patches or upgrades may need to be applied.

However, with a large number and variety of devices, and with each type of device having unique requirements, it can be challenging to keep track of the state (configuration) of each device. For this reason, individual devices can often be missed when it comes to servicing, part replacements and hardware/software upgrades, causing the devices to be incorrectly configured and operate poorly or not at all. Depending on how frequently the device is used, and how detrimental the lack of maintenance is, it can be some time before the configuration error of the device is detected through poor performance, and even then it can be a challenge to determine the exact nature of the configuration error of the device.

Consequently, there is a need for a system that can track the configurations of various medical devices, determine whether a device has a configuration error and the nature of that error.

A document WO2020/254452 A1 discloses a non-transitory computer readable medium that stores instructions readable and executable by at least one electronic processor to perform a suspect device configuration detection method. The method includes: extracting a fleet configuration transactions database of device configuration transactions from device log data and/or system configuration files of a fleet of devices wherein each configuration transaction includes one or more support data fields, a parameter identifier, and its value; constructing a configuration outlier detector to identify outlier configuration transactions in the fleet configuration transactions database; detecting one or more suspect configuration transactions by applying the configuration outlier detector to configuration transactions extracted from one or more devices of interest; and generating at least one of an alarm and a report when the one or more suspect configuration transactions are detected.

Another document EP 3030996 A2 discloses a method that includes obtaining a set of operational properties of an imaging system. The method further includes identifying an operational property of the set of operational properties that intermittently falls outside of a predetermined operational range and does not require immediate service of the imaging system. The method further includes generating a trend for the identified operational property. The method further includes comparing the generated trend with at least one reference trend. The method further includes determining the imaging system should be serviced based on the comparison. The method further includes generating a service notification signal in response to determining the imaging system should be serviced, where the service notification signal invokes service of the imaging system.

A document US 2015/227838 A1 discloses a method of building a model for predicting failure of a machine, including parsing daily machine event logs of one or more machines to extract data for a plurality of features, parsing service notifications for the one or more machine to extract failure information data, creating bags from the daily machine event log data and failure information data for multiple instance learning by grouping daily event log data into the bags based on a predetermined predictive interval, labeling each bag with a with a known failure as positive, and bags without known failures as negative, where a bag is a set of feature vectors and an associated label, where each feature vector is an n-tuple of features, transforming the multiple instance learning bags into a standard classification task form, selecting a subset of features from the plurality of features, and training a failure prediction model using the selected subset of features.

SUMMARY OF THE INVENTION

The invention is defined by the claims.

According to examples in accordance with an aspect of the invention, there is provided an equipment monitoring system comprising:

- a communication module, configured to:
  - receive first telemetry information from a medical device;
  - transmit to the medical device a request for at least second telemetry information, wherein the telemetry information comprises a plurality of system configuration attributes or performance attributes of the medical device, and for each attribute a corresponding value and change date; and
  - receive the second telemetry information from the medical device;
- a memory, configured to store the telemetry information; and
- a processor, configured to:
  - determine whether the medical device has a configuration error based on the first telemetry information, and if the medical device is determined to have the configuration error:
    - instruct the communication module to transmit the request for the second telemetry information; and
    - determine whether the medical device has the configuration error based on the second telemetry information.

The communication module of the equipment monitoring system receives first telemetry information from a medical device. The processor of the equipment monitoring system then determines, based on the first telemetry information, whether the medical device has a configuration error. If it is determined that the medical device does not have the configuration error, no further action need be taken. However, if it is determined that the medical device does have the configuration error, further investigation is required to confirm this finding. To achieve this, the processor causes the communication module to transmit a request for second telemetry information to the medical device.

The first telemetry information may have been generated at a scheduled time, and later transmitted to the equipment monitoring system. Alternatively, the first telemetry information may have been transmitted immediately after generation but the equipment monitoring system might not have analyzed it until some time had passed. In any case, the second telemetry information is newer and more representative of the medical device's state at the current time than the first telemetry information because it is generated by the medical device at the time the medical device received the request for second telemetry information, or at least more recently than when the first telemetry information was generated.

The communication module receives the second telemetry information from the medical device. The processor again determines whether the medical device has the configuration error, this time based on the second telemetry information.

The processor of the equipment monitoring system then generates a notification that the medical device has the configuration error. This notification can include an identification of the device such as a name or serial number, and/or the specific attribute or attributes (and the associated values and/or change dates) that caused the equipment monitoring system to determine that the medical device has the configuration error. The notification might only be generated if the system determines that the device has the configuration error based on the second telemetry information, or optionally based on a combination of the first and second telemetry information. The notification may be sent to an engineer or other personnel responsible for the maintenance of the device.

The processor may be configured to compare the first and/or second telemetry information to telemetry information for one or more similar medical devices, wherein the medical device and similar medical devices share one or more common attributes; and determine that the medical device has the configuration error if the medical device has a value or change date for the common attribute that is different from the one or more similar medical devices.

Similar medical devices are devices that are expected to share at least one attribute that has matching value(s) and/or change date(s) with the medical device. For example, similar medical device will have a same particular component(s) or software element(s), or change date (i.e. date when a change in configuration has been made). In some cases, the similar devices may all be the same make and model device. For example, when a software patch is rolled out, it is expected to be applied to all devices using that software. By comparing the first and/or second telemetry information to telemetry information of similar devices (devices all using the same software), the processor can determine whether the medical device has received the expected patch. If it has, the devices should all have the same value for the common attribute. If the medical device has not been patched, for example if it was accidentally missed, this will be detected because the common attribute will have a different value/change date for the medical device when compared to the similar medical devices.

The processor may be configured to compare the first and/or second telemetry information with a telemetry template; and determine that the medical device has the configuration error if the first and/or second telemetry information does not match the telemetry template, wherein the telemetry template includes one or more of:

- an expected number of values and/or change dates for each attribute;
- an expected value and/or change date for each attribute;
- an expected number of attributes;
- an expected list of attributes; and
- a requirement that at least a first and second attribute have corresponding values and/or change dates.

In this way, the system is able to detect one or more of the following types of configuration error: conflicting information (multiple values for an attribute for which there should be only one), missing information (the absence of an attribute or of a value for an attribute), unstable reports (values changing more often than is expected) and partially completed servicing work.

The processor may be configured to compare the first and/or second telemetry information with earlier telemetry information received from the medical device, to determine a difference between the first and/or second telemetry information and the earlier telemetry information. It may then compare the difference to one or more field change orders (FCOs), wherein the processor is configured to determine that the medical device has the configuration error if the difference does not correspond to the one or more FCOs.

In this way, the system can verify the successful completion of planned work. Planned work is typically documented using a FCO or other similar documentation. FCOs commonly specify the attribute(s) to be modified for the device, the new value(s) and the date(s) that the change is scheduled for. By comparing the difference in device configuration to the FCO(s), the system can verify whether the planned action was successfully implemented, and if it was not, identify the work that remains to be completed.

The processor may be configured to determine a latest-reported date for each attribute absent from the first telemetry information based on previously received telemetry information; compare, for each absent attribute, the latest-reported date to a corresponding expected reporting frequency, wherein the medical device is determined to have the configuration error if the latest-reported date exceeds the corresponding expected reporting frequency, wherein the request for second telemetry information comprises a request for the absent attributes for which the latest-reported date exceeds the corresponding expected reporting frequency, and wherein the processor is further configured to determine whether the second telemetry information includes values for all of the absent attributes that were requested, and determine that that the medical device has the configuration error if the second telemetry information does not include values for all of the absent attributes that were requested.

Some attributes of the medical device are frequently included in telemetry information. Others are only rarely reported. Due to device errors, it is possible for the telemetry information to be incorrectly or incompletely generated, leading to certain attributes not being included. In these cases, it can be difficult to distinguish between an attribute that is simply rarely reported, and a malfunction in the medical device.

By determining a latest (most recent) date that a value for the attribute missing from the first telemetry information was reported, and comparing that to an expected reporting frequency, the system can detect a suspected malfunction in the medical device when the latest reporting date exceeds the expected reporting frequency. This means that the latest reporting date is further in the past than the expected reporting frequency, for example, if an attribute is expected to be reported every two days but the latest-reported date was three days ago, then the latest-reported date exceeds the expected reporting frequency. By transmitting a request for telemetry information including the missing attributes, the system can test the suspected malfunction. If the second telemetry does not include values for each of the missing attributes, the system can determine that the device has the configuration error.

The memory may be configured to store additional data, the additional data comprising one or more of: one or more telemetry templates; earlier telemetry information; one or more field change orders; and a set of expected reporting frequency values.

The processor then generates a notification that the medical device has the configuration error if it determines that the medical device has the configuration error based on the second telemetry information.

The system can generate a notification for a user/engineer, informing them of the configuration error in the device. This may only be done when it is determined that the medical device has the configuration error based on the second telemetry information, as this is the more reliable determination. The notification can include the specific attribute or attributes (and their values and change dates) responsible for the configuration error, as well as a unique identifier for the medical device from which the telemetry information came.

According to examples in accordance with an aspect of the invention, there is also provided a method for determining whether a medical device has a configuration error, the method comprising:

- receiving, by an equipment monitoring system, first telemetry information from the medical device, wherein the first telemetry information comprises a plurality of system configuration attributes or performance attributes of the medical device, and for each attribute a corresponding value and change date;
- determining, by the equipment monitoring system, whether the medical device has the configuration error based on the first telemetry information, and if it is determined that the medical device has the configuration error based on the first telemetry information:
  - transmitting by the equipment monitoring system a request for second telemetry information to the medical device;
  - receiving by the equipment monitoring system the second telemetry information; and
  - determining by the equipment monitoring system whether the medical device has the configuration error based on the second telemetry information.

The method uses the communication module of an equipment monitoring system to receive first telemetry information transmitted by a medical device.

The telemetry information includes at least three fields: an attribute of the device, meaning the name of a variable of the device, for example "driver version"; a value of that attribute, for example the driver version number; and a change date, the date on which the medical device was modified with that value, in this example the day the driver was downloaded on to the medical device.

The equipment monitoring system uses the first telemetry information to determine whether the medical device has the configuration error. This can be done in a variety of different ways. If the equipment monitoring system determines that the medical device has the configuration error, it transmits a request for second telemetry information. The second telemetry information is newer than the first telemetry information, meaning that it was generated by the medical device more recently that the generation of the first telemetry information and is therefore more representative of the true current state of the medical device. The second telemetry information can include all of the same attributes of the first telemetry information, or it can include a sub-set of the attributes of the first telemetry information. The second telemetry information may comprise or consist of attributes not found in the first telemetry information. The attributes to be included in the second telemetry information may be determined by the processor based on the configuration error and included in the request for second telemetry information.

When the equipment monitoring system receives the second telemetry information, it determines whether the medical device has the configuration error based on the second telemetry information. The processor may use the same method as was used for the first telemetry information, or may use a different determining method. If the processor determines that the medical device still has the configuration error, the processor can generated a configuration error notification, which can be sent to an engineer and can specify the configuration error.

By using the first telemetry information to come to an initial conclusion as to whether the medical device has the configuration error, the equipment monitoring system can determine whether the configuration of the medical device requires further investigation. If the first determination step indicates that there is a configuration error, the equipment monitoring system can perform a more thorough inspection of the medical device by obtaining more up-to-date telemetry information. In some cases, this second telemetry information will indicate there is no error in the device at the present time, and no further investigation is required. This can occur for example when the first telemetry information was generated part of the way through an upgrade procedure, and the telemetry information indicates that only a subset of scheduled upgrades have been applied. By obtaining second telemetry information at a later date when the upgrade has completed, the situation is clarified. Alternatively, if the second telemetry information indicates that the configuration error is present in the medical device, there is greater confidence that the error is real, and that the upgrade has failed to fully complete. In some examples of the invention, an engineer can be informed of the error automatically by a notification generated by the equipment monitoring system.

The determining steps may comprise comparing the first and/or second telemetry information to telemetry information for one or more similar medical devices, wherein the medical device and similar medical devices share a common attribute; and determining that the medical device has the configuration error if the medical device has a different value or change date for the common attribute than the one or more similar medical devices.

This is one exemplary method by which a configuration error can be detected. As explained above, similar medical devices are devices that are expected to share a common attribute and corresponding value/change date for that attribute with the medical device. For example, component(s) or software element(s). In some cases, the similar devices may all be the same make and model of device. When an upgrade for, in this example software, is rolled out, it is expected to be applied to all devices using that software. By comparing the telemetry information from the medical device to that from similar medical devices, the system can detect whether the medical device has been upgraded (in which case it will have the same value/change date for the common attribute as is found in the telemetry information for the similar devices), or if it has been missed and has a configuration error (in which case it will not have the same value as the similar medical devices for the common attribute).

The determining steps may comprise comparing the first and/or second telemetry information with a telemetry template; and determining that the medical device has the configuration error if the first and/or second telemetry information does not match the telemetry template, the telemetry template including one or more of:

- an expected number of values and/or change dates for each attribute;
- an expected value and/or change date for each attribute;
- an expected number of attributes;
- an expected list of attributes; and
- a requirement that at least a first and second attribute have corresponding values and/or change dates.

This is a second possible method by which configuration errors can be detected. Deviation of the telemetry information from a telemetry template is indicative of a configuration error. For example, it is common that upgrades to multiple hardware and/or software components in devices must be performed together, due to the interconnected nature of the components. Consequently, for a successful upgrade, the values of multiple attributes should correspond and change in a predictable way. For example, the change dates of attributes that are known to be linked should show the same date, indicating that they have been updated together. Differing change dates indicate that the attributes have not been upgraded together for some reason, such as the medical device being shut down before the upgrades could complete.

The determining steps may comprise comparing the first and/or second telemetry information with earlier telemetry information received from the medical device, to determine a difference between the first and/or second telemetry information and the earlier telemetry information; and comparing the difference to one or more field change orders, wherein the medical device is determined to have the configuration error if the difference does not correspond to the one or more field change orders.

Generally, upgrades or modifications to a device are planned in advance, and documented using a field change order (FCO) or other similar documentation. Comparing current (first and/or second) telemetry information to earlier telemetry information for the same medical device allows the system to identify the differences between the telemetry information. For a successful upgrade/modification, these differences should correspond to the FCO(s) implemented in the time between the generation and transmission of the earlier telemetry information and the generation and transmission of the current telemetry information. Where there is a discrepancy, the system can detect that one or more FCOs has not been correctly implemented and that the medical device has a configuration error.

The determining step may comprise determining, by the equipment monitoring system, a latest-reported date for each attribute absent from the first telemetry information based on previously received telemetry information; and comparing, for each attribute, the latest-reported date to a corresponding expected reporting frequency, wherein the medical device is determined to have the configuration error if the latest-reported date exceeds the corresponding expected reporting frequency, wherein the request for second telemetry information comprises a request for the absent attributes for which the latest-reported date exceeds the corresponding expected reporting frequency.

The second determining step may comprise determining whether the second telemetry information includes values for all of the absent attributes requested; and determining that that the medical device has the configuration error if the second telemetry information does not include values for all of the absent attributes requested.

Depending on the medical device, telemetry information may be transmitted infrequently, or might only include certain attributes most of the time. This can lead to the values of certain attributes being updated only infrequently. At the same time, sometimes problems can arise in the medical device that stop telemetry information being properly generated and/or transmitted, meaning that some attributes and their values are not reported in the telemetry information when they should have been. By determining a latest-reported date for attributes missing from the first telemetry information, and comparing these latest-reported dates to an expected reporting frequency, the system can distinguish between an attribute that is simply rarely reported, and a suspected malfunction in the medical device.

The request for second telemetry information includes a request for the absent attributes for which the latest-reported date exceeds the corresponding expected reporting frequency. This tests the medical device. If the second telemetry information includes values for each of the requested attributes, there is no immediate malfunction. However, if the second telemetry information does not include values for all of the requested attributes, the system determines that the medical device has the configuration error.

The equipment monitoring system generates a notification that the medical device has the configuration error if it determines that the medical device has the configuration error based on the second telemetry information.

The equipment monitoring system can generate a notification that the medical device has the configuration error only after the configuration error has been confirmed using the second telemetry information. The notification can include a unique identifier for the device, such as a serial number or an assigned name. The notification can also include the specific attribute or attributes (and the associated values and/or change dates) that caused the equipment monitoring system to determine that the medical device has the configuration error. The notification can be sent to an engineer.

According to examples in accordance with an aspect of the invention, there is also provided a computer program comprising computer program code means which is adapted, when said program is run on processors of an equipment monitoring system, to implement the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
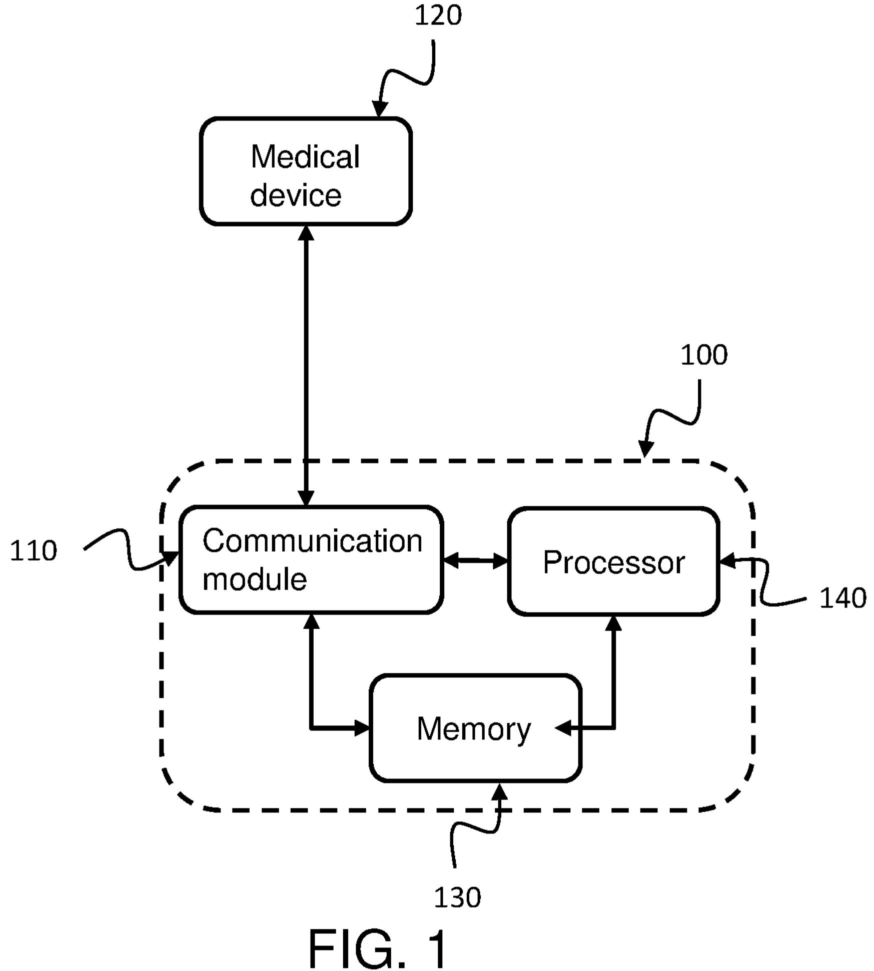
FIG. 1 shows an example of an equipment monitoring system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an equipment monitoring system. An exemplary equipment monitoring system will be described with reference to FIG. 1.

The equipment monitoring system 100 (referred to herein as "the system") comprises a communication module 110, a memory 130 and a processor 140. The communication module 110 communicates with a medical device 120 (also referred to as "the device"), receiving from the device 120 first telemetry information. The communication module 110 can also transmit to the device 120 a request for second telemetry information, and can receive from the device 120 the second telemetry information.

Telemetry information can include system configuration information and performance data, but does not include personal information regarding patients or staff, or marketing information. The telemetry information reflects the current configuration of the device 120, or at least the configuration of the device 120 at the time of the creation of the telemetry information. A non-exhaustive list of examples of telemetry information includes operating system type and version, component serial numbers, driver versions and BIOS versions.

Telemetry information comprises at least the three following data points: an attribute (for example "BIOS" or "driver version"), a value for that attribute (in the example of driver version, this would be the version number), and a change date for that value (the date that this value was first recorded by the device 120). Telemetry information can be generated by the device 120 daily, although it may be generated more or less frequently. The telemetry information can contain only a subset of all of the attributes of the device 120.

The memory 130 stores the first and second telemetry information.

The processor 140 determines, based on the first telemetry information, whether the device 120 has a configuration error based on the first telemetry information. The processor 140 can cause the communication module 110 to transmit the request for second telemetry information to the device 120. After receipt of the second telemetry information, the processor 140 determines whether the device 120 has the configuration error based on the second telemetry information, or a combination of the first and second telemetry information.

Often, the volume of telemetry data gathered for a set of medical devices 120 over the course of even one day is too large to be processed by humans. In settings such as hospitals, which have a large number of devices 120, all of which are important to maintain, configuration errors in medical devices 120 can go undetected by for a substantial length of time even though the devices 120 may be frequently generating telemetry information indicative of a configuration error. This is particularly true for devices 120 that are not frequently used. Some configuration errors impact the performance of the devices 120 in ways that are not immediately obvious to their operators, meaning that even if the device 120 is frequently used, the configuration error may still go undetected for a long time.

Common types of configuration errors include: conflicting information, where a device 120 reports multiple values for an attribute that should have only one value; missing information, where certain key attributes are reported without any value or are not reported at all; unstable reports, where attributes that should have values that change at a stable frequency are reporting changing values and a much higher frequency or lower frequency than expected, or with an inconsistent/fluctuating frequency; unusually high data volume, where a medical device 120 is transmitting telemetry information more frequently than is expected; truncated information, where values or change dates are only partially reported in the telemetry information; and incorrect telemetry information, where it is known that the device has a certain attribute value and change date, but the telemetry information is reporting a different value and/or change date. These configuration errors make the telemetry information gathered for a device 120 less useful, invalid or even dangerous to rely upon, and are indicative of a problem with the device 120.

Today, the normal response to identifying an error in a device 120 is to raise an alert/notification, to which a human response is required to resolve the issue. However, as mentioned above, it is very likely that the error will go undetected for a long time, and often will only be detected when the device 120 visibly malfunctions. At this stage a fast response is usually required, which is complicated by not knowing the cause of the malfunction. The stored telemetry information can be reviewed by the engineer to help identify the problem, but this can be a time consuming process.

By automating the analysis of the telemetry information, configuration errors can be detected more quickly and more consistently, as well as before critical failures occur. Additionally, the specific attributes, values and change dates responsible for the configuration error can be communicated by the communication module 110 to an engineer responsible for fixing the device, making it easier to correct the issue. This notification to the engineer can include any one or combination of: a current time and date; the first and/or second telemetry information; a unique identifier for the device 120; the attribute, value and/or change date that caused the system to determine that there was a configuration error.

In some instances, telemetry information can indicate a configuration error in a device 120 when in reality no error is present. For example, if the automatic generation of the telemetry information occurred part way through the application of a software upgrade to a group of devices, then some devices might not yet have finished upgrading and will report old attribute values. For this reason, when the system 100 determines that the device 120 has a configuration error based on the first telemetry information, it sends an instruction to the device 120 to transmit second telemetry information. The second telemetry information is generated by the medical device 120 when it receives the instruction, meaning that it is the most up-to-date representation of the device's configuration. If the system 100 determines that there is no configuration error based on the second telemetry information, it can conclude that there is no configuration error in the device 100 and will not transmit a notification of an error. In this way, a false positive identification of a configuration error can be mitigated.

If the system 100 determines, based on the second telemetry information, that the device 120 does have the configuration error, then there can be more confidence that this is a real configuration error. The most up-to-date configuration information for the device 120 can be included in a notification to an engineer that specifies that the device 120 has an error. Importantly, problems can be detected as soon as the system 100 receives and processes the telemetry information.

In some examples, the processor 140 is configured to compare the first and/or second telemetry information from the medical device 120 to telemetry information one or more similar medical devices in order to determine whether the device 120 has the configuration error. Preferably, a similar medical device is the same type of device (same make and model) as device 120. A similar medical device must at least share one common attribute, such as components or software elements, with the medical device 120.

This can be useful in detecting devices 120 that have been missed in scheduled upgrade or maintenance activities. If a number of similar devices have been upgraded (for example, according to a field change order specifying a software update for a common software attribute), it is possible that a device 120 will be missed and not receive the upgrade. The system 100 can detect this situation by comparing the telemetry from a number of devices that share the common attribute to be upgraded. The system 100 can detect that the device 120 has a different value and change date for the common attribute that the other devices, meaning that the device 120 has not been upgraded. This can be further investigated by requesting second telemetry information from the device 120. In some cases, the second telemetry information will show that in the time between the generation of the first telemetry information and the later analysis by the system 100, the upgrade was applied and there is no configuration error. Alternatively, the error may persist, in which case there can be high confidence that the error is real and a notification may be sent to an engineer.

In some examples, the processor 140 can compare the first telemetry information to a telemetry template. This template can be specific to the type of device 120 transmitting the telemetry information. The template can specify: an expected number of values and/or change dates for each attribute; an expected value and/or change date for each attribute; an expected number of attributes; an expected list of attributes; and a requirement that at least a first and second attribute have corresponding values and/or change dates.

By comparing the telemetry information to the telemetry template, conditions such as missing information or conflicting information can be identified. If the processor 140 determines that the telemetry information is, for example, missing information, it can instruct the communications module 110 to transmit a request for second telemetry information. In particular, the request can include an instruction that the second telemetry information includes the missing attribute, its value and change date. If the second telemetry information includes the missing information, the system 100 can determine that there is no configuration error.

In some cases, a series of changes may be made over a short space of time. The components of a device 120 do not operate in isolation, instead they interact with other components within the device 120. When a first component undergoes a change, it is common that a second component that interacts with the first component will also undergo a change. The telemetry template can link two or more attributes, such that they are required to have corresponding values and/or change dates. In this way, if an upgrade is applied to the first component but the second component (linked to the first component) is not also upgraded, the system 100 can detect this unusual service action. The system 100 may flag it for review by a human if the second telemetry information confirms that the attributes do not have the required corresponding values and/or change dates.

In some examples, a device 120 can be upgraded by replacing a first component with a second component that reports under a different name (meaning that it has a different attribute name). For example, in Computed Tomography devices a back projector (BP) can be replaced with a next generation back projector (NGBP). After this upgrade, the telemetry information for the device 120 may include both a BP attribute and a new NGBP attribute, despite the NGBP replacing the BP. This error can be detected by the system 100 because the change date for the BP attribute will no longer advance, whereas the NGBP change date will continue to change over time with additional upgrades/patches. In such a circumstance, a rule may be applied by the system 100 such that the processor 140 hides the BP telemetry information and does not consider it when determining a configuration error when the telemetry information also includes an NGBP attribute. The telemetry information may include, for each attribute, an associated function carried out by that attribute. Alternatively, the system 100 may be encoded with the function information for each possible attribute. Where two attributes are included in the telemetry information that perform the same function, the system 100 may hide the attribute with the oldest change date and only process the attribute with the newest change date.

In some circumstances, instead of replacing an old component like a BP with a new component like a NGBP, the old component may be removed and its functionality assumed by an already present component. In the BP example, this could be an already present graphics processing unit (GPU). The telemetry information generated by the device 120 may then specify that the GPU now performs the functions of the BP. Alternatively, the system 100 or telemetry template may be updated to include this information. In either case, the system 100 can again hide the BP telemetry information in favour of the GPU telemetry information.

In some examples, the processor 140 compares the first telemetry information to earlier telemetry information received from the same medical device 120. Preferably, this earlier telemetry information is the latest (most recent) telemetry information that was received prior to the receipt of the first telemetry information. The difference between the two sets of telemetry information is determined, indicating how the configuration of the device 120 has changed in the period between the generation of the two sets of telemetry information. The difference is then compared to an FCO. If the difference corresponds to the changes listed in the FCO, then the changes were successfully implemented. However, if there is a discrepancy between the difference and the FCO then the changes listed in the FCO were not successfully or fully implemented, or there is some other error in the device 120. To confirm this, the system 100 can send a request for second telemetry information to the device 120. Once the system 100 receives the second telemetry information, the second telemetry information can be compared to the earlier telemetry information and/or the first telemetry information. The difference between the second telemetry information and the earlier (and/or first) telemetry information can again be compared to the FCO. If there is still a discrepancy then it is likely that there is a genuine configuration error.

Where multiple FCOs have been implemented in the time between the generation of the earlier telemetry information and the first telemetry information, and particularly where the changes relate to the same attribute(s), it can be challenging to determine whether all of the changes were applied because the first telemetry information will only report the current attribute value and change date. In these cases, the system 100 may send a notification to an engineer including the first telemetry information and the FCOs for review. It is likely that the Engineer will be able to tell from the first telemetry information in its entirety whether all of the FCO changes have been implemented.

Not all attributes of the device 120 are included in the telemetry information all of the time. While telemetry information may, in some examples, be generated every day, some attributes might only feature in the telemetry information once every two days, once a week or once a month (for example). Consequently, it can be difficult to distinguish between telemetry information that is indicative of an error due to missing information and normal telemetry information that does not include an infrequently reported attribute. In some examples, the processor 140 is configured to determine a latest-reported date for each attribute absent from the first telemetry information by analyzing earlier telemetry information. To this end, the memory 130 can store previously received telemetry information. The memory 130 can store, for each attribute, an expected reporting frequency. For example, the expected reporting frequency of the patch version for a device 120 is three days. When the system 100 receives first telemetry information for the device 120 that does not include the patch version attribute, it determines the last time it received telemetry information for the device 120 that did include the patch version attribute (the latest-reported date of the patch version attribute). If this was greater than three days ago then the patch value configuration data is overdue, and its absence is indicative of a configuration error. The system 100 can transmit, via the communication module 110, a request for second telemetry information. More specifically, it can transmit a request for the overdue configuration data. If the second telemetry information still does not include the overdue configuration data then there is likely a genuine error in the device 120.

The invention also provides a method for determining whether a medical device 120 has a configuration error. An exemplary method 200 will be described with reference to FIG. 2.

In step 210, the system 100 receives the first telemetry information from the medical device 120. In step 220 the system 100 determines whether the medical device 120 has a configuration error using the first telemetry information. If the system 100 determines that there is a configuration error, in step 230 it requests second telemetry information from the device 120. In step 240, the system 100 receives the second telemetry information from the device 120. In step 250, the system 100 determines whether the medical device 120 has the configuration error using the second telemetry information. If the system 100 determines that the configuration error is present, it may proceed to step 260 in which a notification is generated and sent to an engineer or other maintenance/servicing personnel.

In some examples, the determining 240 is based on both the first and second telemetry information.

Variations of the determining steps 220 and 250 will now be explained with reference to FIG. 3. In one example, the determining 220 may comprise comparing 221 the first telemetry information to telemetry information for one or more similar devices (defined above) and determining 222 that the medical device 120 has a configuration error if the device 120 has a different value and/or change date for a common attribute shared with the similar devices. Similarly, the determining 250 can comprise comparing 251 the second telemetry information to telemetry information for one or more similar devices and determining 252 that the medical device 120 has a configuration error if the device 120 has a different value or change date for a common attribute shared with the similar devices. The request for second telemetry information transmitted 230 by the system 100 to the device 120 can specify that the second telemetry information must include at least the common attributes of the device 120 with values that do not match the values of the similar devices.

An example of this method will now be outlined. Consider a group of ten identical devices. Because the devices are identical, they are expected to have all of the same attributes and should have the same values for those attributes (meaning that all of the attributes are common attributes). If nine of the devices (devices one through nine) undergo a software patch, but one device (device ten) is missed, this can be detected using the above method. The system 100 will compare the first telemetry information for device ten with the telemetry information for devices one through nine, comparing all of the values and/or change dates for the common attributes of the devices (in this case, all of the attributes). As the software version of device ten does not match the software version of the other nine devices, the system 100 will determine that device ten has a configuration error at least due to the "software version" attribute. To verify this, the system 100 then requests second telemetry information from device ten (requesting device then to generate and send new telemetry information) including at least the software version attribute, and any other common attributes with values and/or change dates not matching the other nine devices. If, after comparing the second telemetry information to the telemetry information for the other devices, the software version attribute value for device ten still does not match the software version attribute values of the other devices, the configuration error has been confirmed. The system 100 may then generate 260 and send a notification to an engineer or other personnel that identifies device ten and lists the common attribute(s) that the determination of the configuration error are based on.

Figure 3:
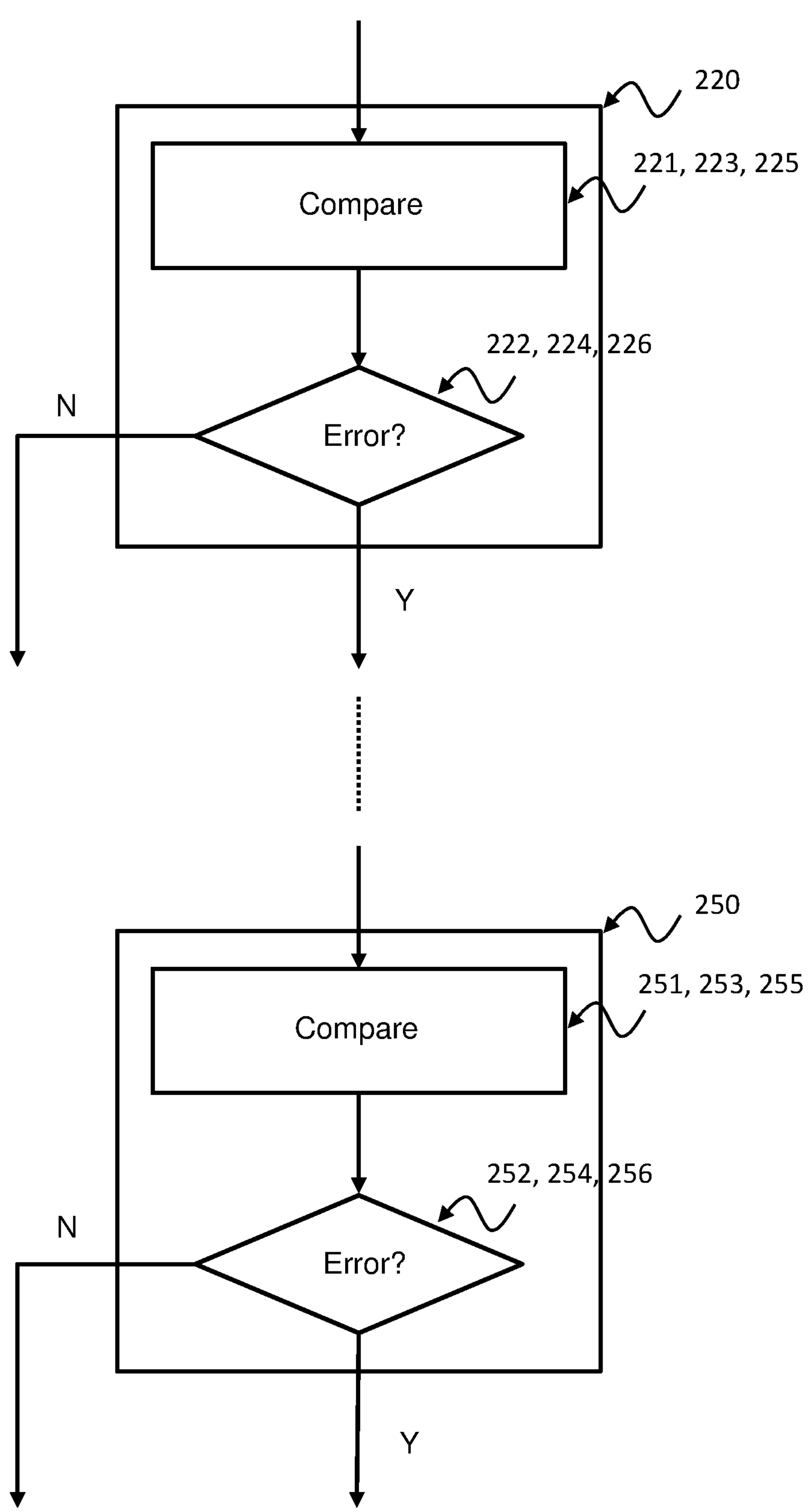
FIG. 3 is a flow diagram depicting variations of a part of an exemplary method.

In another example depicted in FIG. 3, the determining 220 may comprise comparing 223 the first telemetry information with a telemetry template, and determining 224 that the medical device 120 has a configuration error if the first telemetry information does not match or correspond to the telemetry template. Similarly, the determining 250 may comprise comparing 253 the second telemetry information with a telemetry template, and determining 224 that the medical device 120 has the configuration error if the second telemetry information does not match or correspond to the telemetry template. The request for second telemetry information transmitted 230 by the system 100 can specify that the second telemetry information must include at least the attributes (and their value(s) and change date(s)) of the device 120 that were determined 220 to not match or correspond to the telemetry template.

In another example depicted in FIG. 3, the determining 220 may comprise comparing 225 the first telemetry information with earlier telemetry information received by the system 100 from the same medical device 120 in order to determine a difference between the first and earlier telemetry information; and comparing 226 the difference to a FCO. If the difference matches the FCO, then the system 100 can determine that the device 120 does not have the configuration error. However, if the difference does not match the FCO then the system 100 can determine that the device 120 does have the configuration error. Similarly, the determining 250 may comprise comparing 255 the first second information with earlier telemetry information for the same medical device 120 in order to determine a difference between the first and earlier telemetry information, and comparing 256 the difference to a FCO. Again, if the difference matches the FCO then the system 100 can determine that the device 120 does not have the configuration error, and if the difference does not match the FCO then the system 100 can determine that the device 120 does have the configuration error The difference between the first or second telemetry information and the earlier telemetry information can include at least a list of the attributes with values and/or change dates that change between the two sets of telemetry information, and the most recent values and/or change dates for those attributes (the values/change dates reported in the first and/or second telemetry information). Comparing the difference to one or more FCOs can comprise determining whether all of the attributes marked for change in the FCO are included in the difference list, and determining if the attribute values and/or dates in the difference list match the values and/or dates listed in the FCO. The request for second telemetry information transmitted 230 by the system 100 to the device 120 can specify that the second telemetry information must include at least the attributes (and their value(s) and/or change date(s)) in the difference list, and optionally all of the attributes listed in the FCO. In a preferred embodiment, the request specifies that the second telemetry information must include attributes marked for change in the FCO but that are not present in the difference (in other words, the attributes that should have been changed according to the FCO but have not been changed according to the first telemetry information). The earlier telemetry information may be the telemetry information received most recently prior to the receipt of the first telemetry information.

An example of this method will now be outlined. Consider a device 120 that today transmitted first telemetry information to the system 100, and prior to that most recently transmitted telemetry information to the system 100 five days ago. In the time between the generation and transmission of these two sets of telemetry information, the device 120 was scheduled to undergo a set of changes specified in a FCO—a software patch and a component upgrade. However, the software patch was not applied. By comparing 225 the first telemetry information and the earlier telemetry information (from five days ago), the system 100 determines the difference between the first telemetry information and the earlier telemetry information—that one of the component attributes has a new change date and a new value. The difference is then compared to the FCO, from which it is determined that the difference does not fully correspond to the FCO in that the software attribute is not included in the difference. The system 100 can then transmit 230 an instruction to the device 120 to generate and transmit second telemetry data including at least the software attribute. The system 100 can then compare 256 the second telemetry information to the earlier telemetry information to find the difference between the two, and compare that difference to the FCO. If, by chance, the first telemetry information had been generated after the component replacement but before the software patch had been applied, the second telemetry information would reveal that the software patch had since been applied and the device 120 did not have the configuration error. However, if the difference between the second telemetry information and the earlier telemetry information still does not match the FCO (meaning that the software patch still has not been applied), then the system 100 can determine 250 that the device 120 has the configuration error. The system 100 may then generate 260 and send a notification to an engineer or other personnel informing them of the configuration error. The notification can include any one or combination of an identification of the device 120, the FCO, the difference between the first or second telemetry information and the earlier telemetry information, the first telemetry information, the second telemetry information, the earlier telemetry information. Preferably, the notification will include at least the second telemetry information, the FCO and an identification of the device 120.

Figure 4:
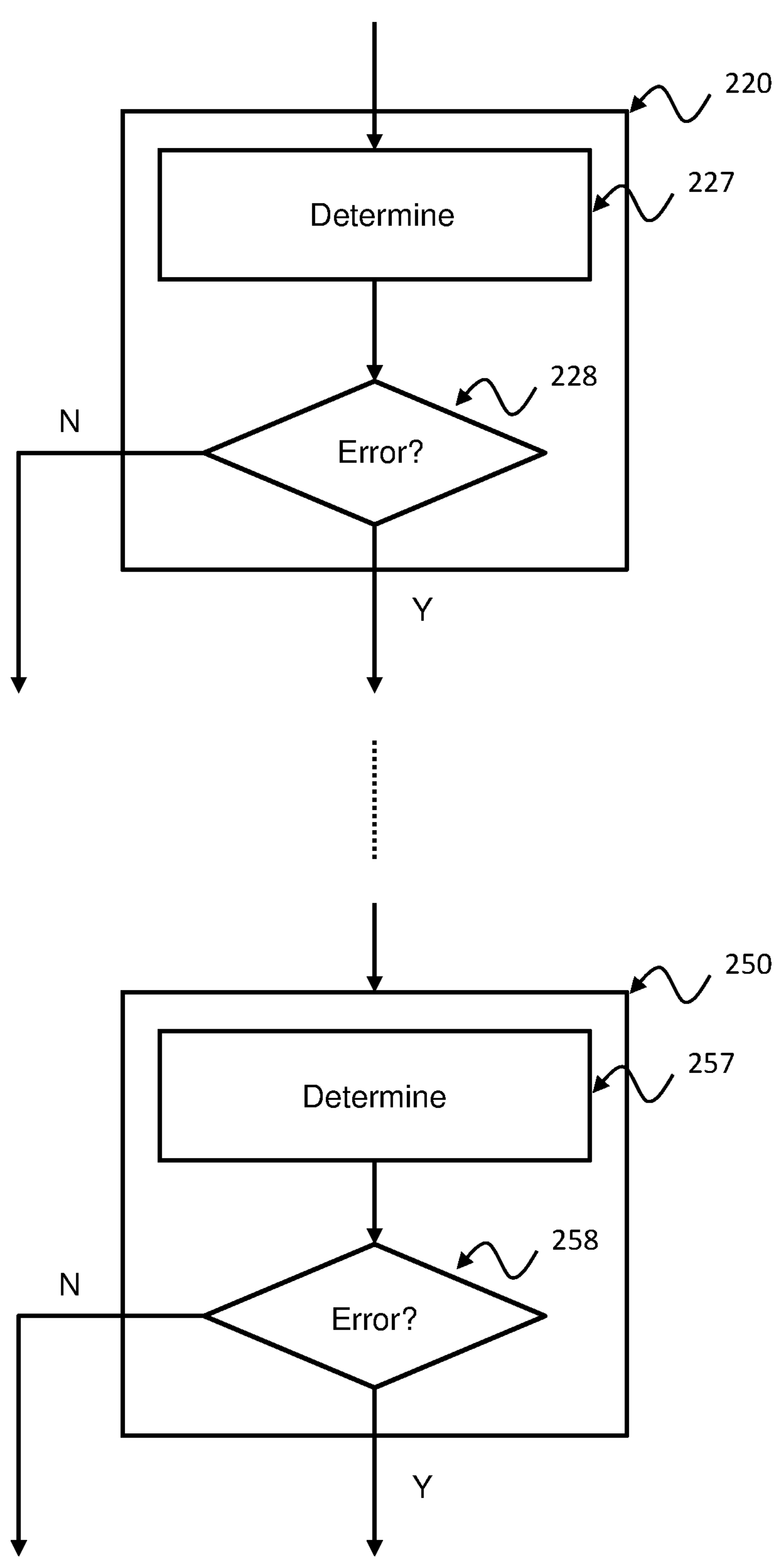
FIG. 4 is a flow diagram depicting another variation of a part of an exemplary method.

As depicted in FIG. 4, the determining 220 may comprise determining 227 a latest-reported date for each attribute absent from the first telemetry information, and comparing 228 said latest-reported date for each attribute to an expected reporting frequency. If the system 100 finds that the latest-reported date for an attribute exceeds the expected reporting frequency (meaning that the attribute is overdue—it has not been reported for longer than is expected), the system 100 can determine that the device 120 has an error and instruct the device 120 to generate and send second telemetry data including at least the overdue attributes. The determining 250 can comprise determining 257 whether the second telemetry information includes all of overdue attributes, and determining 258 that the device 120 has the configuration error if any of the overdue attributes are missing from the second telemetry information, or if they are reported without a value and/or change date.

In any of the methods described above and depicted in FIGS. 2-4, the request for second telemetry information transmitted 230 by the system 100 to the device 120 can require the device 120 to generate new telemetry information at the time of receipt of the request. The request may specify that the second telemetry information should include all possible attributes of the device, the same attributes as were included in the first telemetry information or the earlier telemetry information, or only the attributes that the system 100 has determined are indicative of the configuration error.

Figure 2:
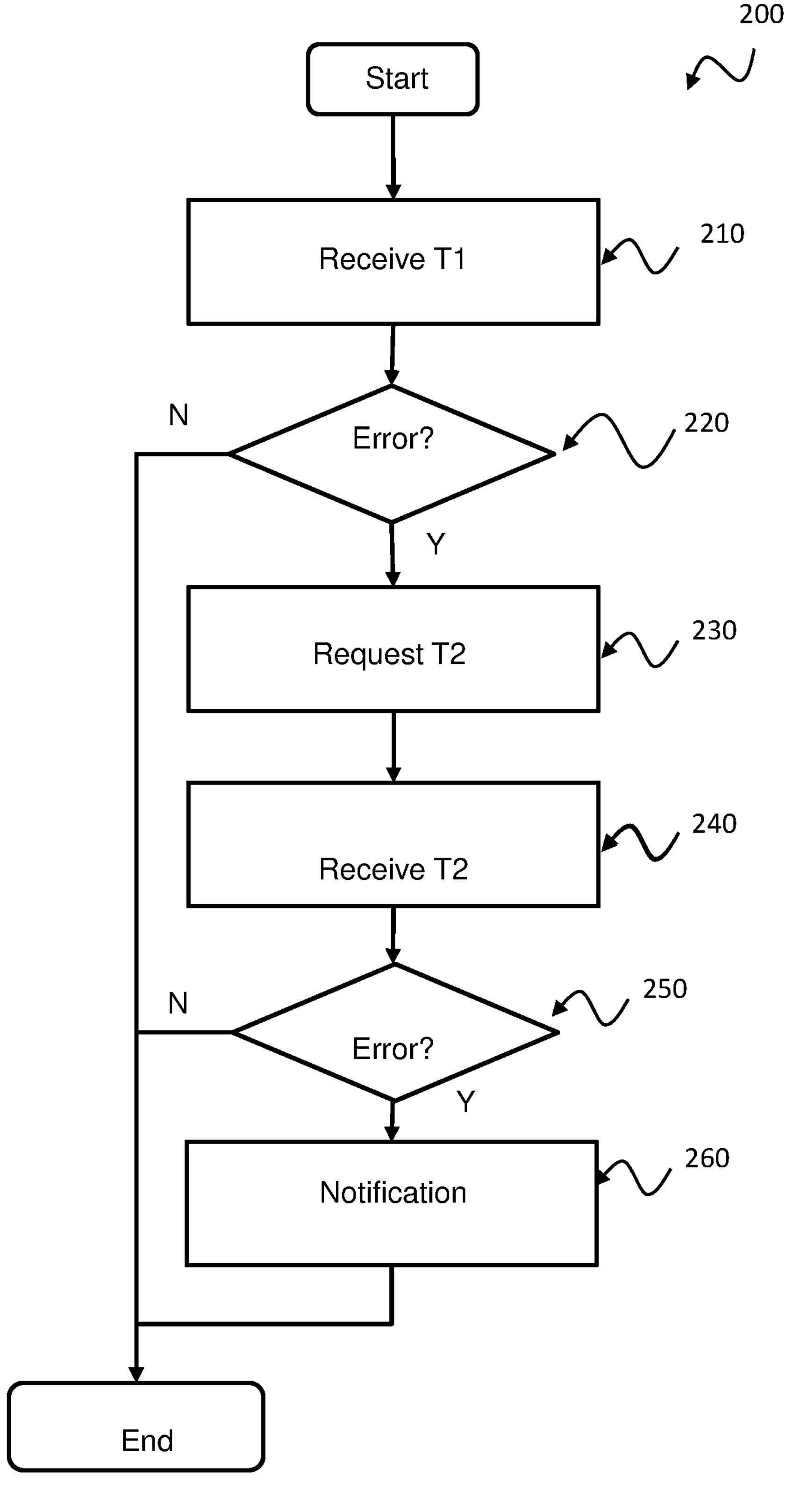
FIG. 2 is a flow diagram depicting an exemplary method.

Any combination of the determining step 220 and the determining step 250 depicted in FIGS. 2-4 and described above can be implemented. For example, in determining step 220 the system 100 may determine if any attributes missing from the first telemetry information are overdue (referring to steps 227 and 228), and in determining step 250 the system 100 may compare the second telemetry information to telemetry information for one or more similar devices (referring to steps 251 and 252).

In another example, in step 220 the system 100 may compare the difference between the first telemetry information and earlier telemetry information to an FCO (referring to steps 225 and 226). As mentioned above, if multiple changes have been made to a single attribute, it can be difficult to determine that all of the changes have been successfully applied because the first telemetry information will only report the most recent attribute value for each attribute. In this case, the difference will not correspond fully to the FCO, as it will not include the intermediate upgrade steps. In step 250, the system 100 may compare the second telemetry information to telemetry information for a similar device (referring to steps 251 and 252). Preferably the similar device is the same make and model device as device 120, and/or it is known that the FCO was fully and successfully implemented for the similar device. Preferably, the second telemetry information will include all of the attributes found in the first telemetry information or the telemetry information for the similar device. If the second telemetry information reports all of the same attribute values and/or change dates as the telemetry information for the similar device then we can have more confidence that all of the steps of the FCO were successfully applied. This is in part because, as mentioned above, often changes to one attribute require changes to other related attributes. If these related attribute changes have been made (detectable in both steps 220 and 250), we can have more confidence that the corresponding hidden attribute changes were made.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. An equipment monitoring system, comprising:
- a communication module, configured to:
  - receive first telemetry information from a medical device;
  - transmit to the medical device a request for at least second telemetry information, wherein the telemetry information comprises a plurality of system configuration attributes or performance attributes of the medical device, and for each attribute a corresponding value and change date; and
  - receive the second telemetry information from the medical device;
- a memory, configured to store the telemetry information; and
- a processor, configured to:
  - determine whether the medical device has a configuration error based on the first telemetry information, and if the medical device is determined to have a configuration error:
    - instruct the communication module to transmit the request for the second telemetry information; and
    - determine whether the medical device has the configuration error based on the second telemetry information; and
- wherein the processor is further configured to generate a notification that the medical device has the configuration error if it determines that the medical device has the configuration error based on the second telemetry information.

2. The system of claim 1, wherein the processor is configured to:
- compare the first and/or second telemetry information to telemetry information for one or more similar medical devices, wherein the medical device and the similar medical devices share a common attribute; and
- determine that the medical device has the configuration error if the medical device has a different value or change date for the common attribute than the one or more similar medical devices.

3. The system of claim 1, wherein the processor is configured to:
- compare the first and/or second telemetry information with a telemetry template; and
- determine that the medical device has the configuration error if the first and/or second telemetry information does not match the telemetry template, wherein the telemetry template includes one or more of:
  - an expected number of values and/or change dates for each attribute;
  - an expected value and/or change date for each attribute;
  - an expected number of attributes;
  - an expected list of attributes; and
  - a requirement that at least a first and second attribute have corresponding values and/or change dates.

4. The system of claim 1, wherein the processor is configured to:
- compare the first and/or second telemetry information with earlier telemetry information received from the medical device, to determine a difference between the first and/or second telemetry information and the earlier telemetry information; and
- compare the difference to one or more field change orders, wherein the processor is configured to determine that the medical device has the configuration error if the difference does not correspond to the one or more field change orders.

5. The system of claim 1, wherein the processor is configured to:
- determine a latest-reported date for each attribute absent from the first telemetry information based on previously received telemetry information;
- compare, for each absent attribute, the latest-reported date to a corresponding expected reporting frequency, wherein the medical device is determined to have the configuration error if the latest-reported date exceeds the corresponding expected reporting frequency, wherein the request for second telemetry information comprises a request for the absent attributes for which the latest-reported date exceeds the corresponding expected reporting frequency, and wherein the processor is further configured to:
- determine, whether the second telemetry information includes values for all of the absent attributes that were requested; and determine that that the medical device has the configuration error if the second telemetry information does not include values for all of the absent attributes that were requested.

6. The system of claim 1, wherein the memory is further configured to store additional data, the additional data comprising one or more of:

one or more telemetry templates;

earlier telemetry information;

one or more field change orders; and a set of expected reporting frequency values.

7. A method for determining whether a medical device has a configuration error, the method comprising:

receiving, by an equipment monitoring system, first telemetry information from the medical device, wherein the first telemetry information comprises a plurality of system configuration attributes or performance attributes of the medical device, and for each attribute a corresponding value and change date;

determining, by the equipment monitoring system, whether the medical device has the configuration error based on the first telemetry information, and if it is determined that the medical device has the configuration error based on the first telemetry information:

transmitting by the equipment monitoring system a request for second telemetry information to the medical device;

receiving by the equipment monitoring system the second telemetry information; and determining by the equipment monitoring system whether the medical device has the configuration error based on the second telemetry information;

wherein the equipment monitoring system generates a notification that the medical device has the configuration error if it determines that the medical device has the configuration error based on the second telemetry information.

8. The method of claim 7, wherein the determining comprises:

comparing the first and/or second telemetry information to telemetry information for one or more similar medical devices, wherein the medical device and similar medical devices share a common attribute; and determining that the medical device has the configuration error if the medical device has a different value or change date for the common attribute than the one or more similar medical devices.

9. The method of claim 7, wherein the determining comprises:

comparing the first and/or second telemetry information with a telemetry template; and determining that the medical device has the configuration error if the first and/or second telemetry information does not match the telemetry template, the telemetry template including one or more of:

an expected number of values and/or change dates for each attribute;

an expected value and/or change date for each attribute;

an expected number of attributes;

an expected list of attributes; and a requirement that at least a first and second attribute have corresponding values and/or change dates.

10. The method of claim 7, wherein the determining comprises:

comparing the first and/or second telemetry information with earlier telemetry information received from the medical device, to determine a difference between the first and/or second telemetry information and the earlier telemetry information; and comparing the difference to one or more field change orders, wherein the medical device is determined to have the configuration error if the difference does not correspond to the one or more field change orders.

11. The method of claim 7, wherein the determining comprises:

determining, by the equipment monitoring system, a latest-reported date for each attribute absent from the first telemetry information based on previously received telemetry information; and comparing, for each attribute, the latest-reported date to a corresponding expected reporting frequency, wherein the medical device is determined to have the configuration error if the latest-reported date exceeds the corresponding expected reporting frequency, wherein the request for second telemetry information comprises a request for the absent attributes for which the latest-reported date exceeds the corresponding expected reporting frequency, and wherein the determining comprises:

determining whether the second telemetry information includes values for all of the absent attributes requested; and determining that that the medical device has the configuration error if the second telemetry information does not include values for all of the absent attributes requested.

* * * * *